United States Patent [19]
Van den Berg et al.

[11] Patent Number: 5,393,399
[45] Date of Patent: Feb. 28, 1995

[54] AMPEROMETRIC MEASURING DEVICE HAVING AN ELECTROCHEMICAL SENSOR

[75] Inventors: Albert Van den Berg, Neuchatel; Alain Grisel, Lausanne, both of Switzerland; Martial Archenault, Lyons, France

[73] Assignee: Gie Cylergie, Nanterre, France

[21] Appl. No.: 117,872

[22] Filed: Sep. 7, 1993

[30] Foreign Application Priority Data

Sep. 7, 1992 [FR] France ................... 9210740

[51] Int. Cl.6 ................... G01N 27/26; G01N 27/404
[52] U.S. Cl. ................... 204/412; 204/153.17; 204/409; 204/415
[58] Field of Search ................... 204/153.17, 415, 412, 204/431, 432, 409

[56] References Cited

U.S. PATENT DOCUMENTS

| 3,791,953 | 2/1974 | Minushkin et al. | 204/422 |
| 4,571,292 | 2/1986 | Liu et al. | 204/412 |
| 4,694,834 | 9/1987 | Meyerhoff et al. | 204/431 |
| 4,851,088 | 7/1989 | Chandrasekhar et al. | 204/415 |
| 4,948,490 | 8/1990 | Venkatasetty | 204/412 |
| 5,120,420 | 6/1992 | Nankai et al. | 204/415 |
| 5,126,034 | 6/1992 | Carter et al. | 204/431 |

FOREIGN PATENT DOCUMENTS

| 0299779 | 1/1989 | European Pat. Off. . |
| 0299780 | 1/1989 | European Pat. Off. . |
| 0328640 | 8/1989 | European Pat. Off. . |
| 8809500 | 12/1988 | WIPO . |

*Primary Examiner*—T. Tung
*Attorney, Agent, or Firm*—Weil, Gotshal & Manges

[57] ABSTRACT

An amperometric sensor device comprises in combination a sensor (21) having a planar structure obtained by photolithographic techniques and a circuit (22) for measuring the intensity of the electrochemical current generated by the sensor (21). The planar structure has an insulating substrate (23 to 25) and a set of electrodes composed of a working electrode (29), a counter electrode (30) and a reference electrode (31). A diffusion membrane (32) is deposited on the working electrode (29). Connection means (26) are provided to connect the electrodes (29,30,31) to the measuring circuit (22). According to the invention, the active conducting part of the working electrode (29), situated at the surface of the substrate (23) is entirely covered by the diffusion membrane (32) which overlaps this electrode (29) over its entire peripheral zone, whereas this membrane is entirely exposed so that, during the operation of the device (20) it is in contact with the fluid to be analysed over its entire surface.

The invention has applications in measuring the content of an oxygen reducible substance in a fluid, notably of chlorine in drinking water.

12 Claims, 7 Drawing Sheets

Fig.1
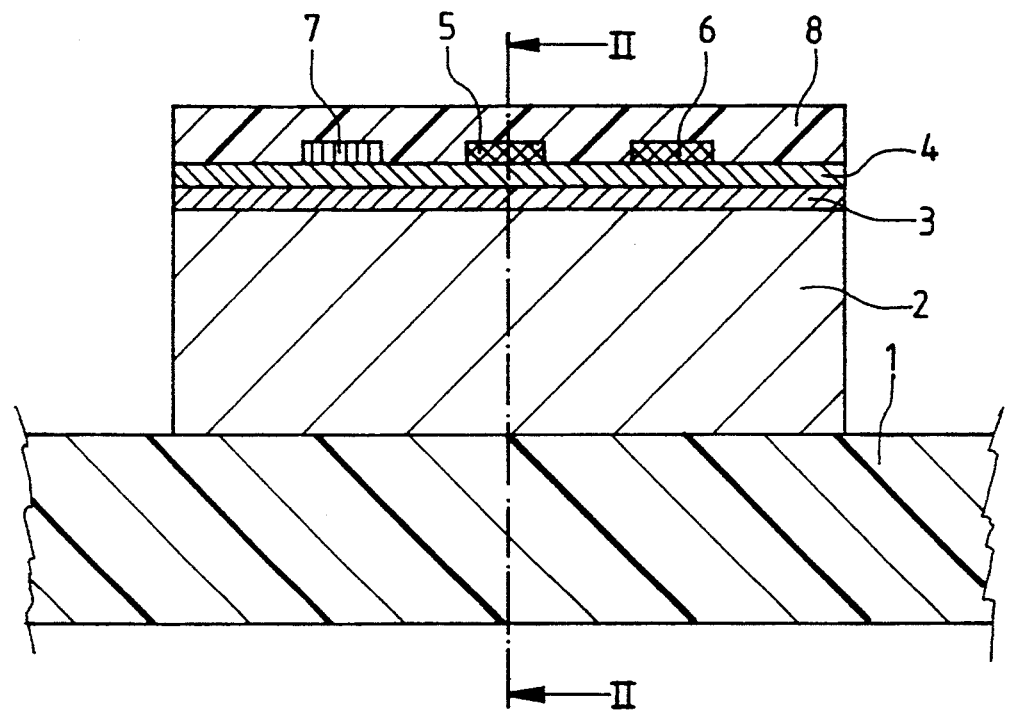
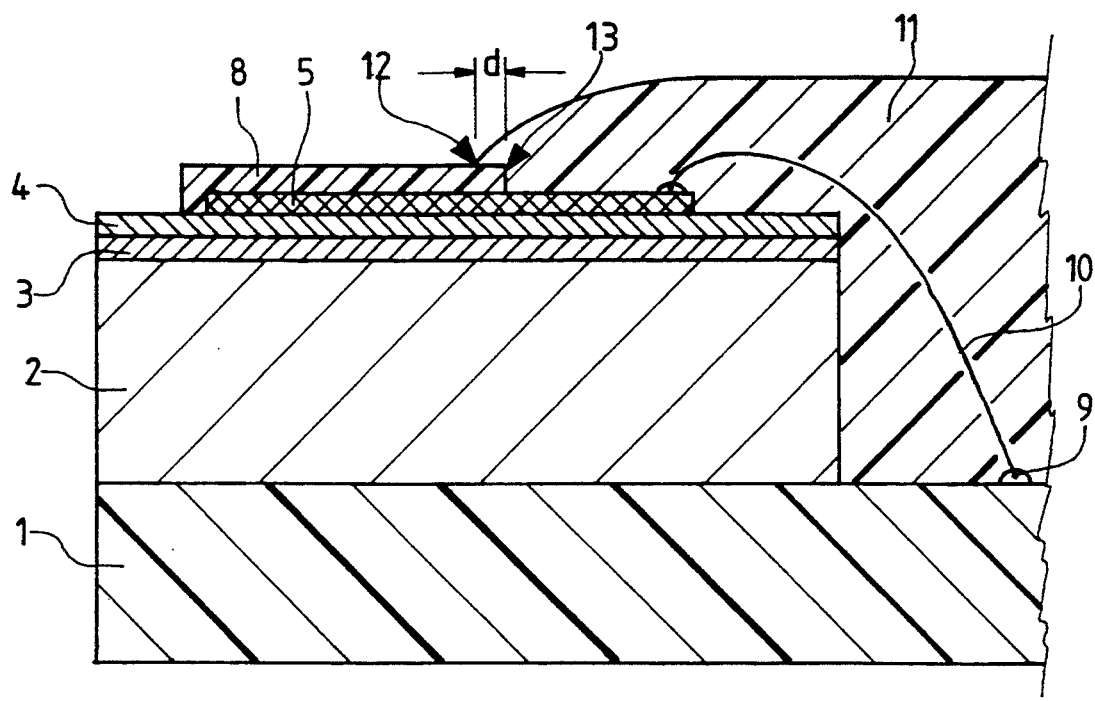
Fig.2

Fig. 8
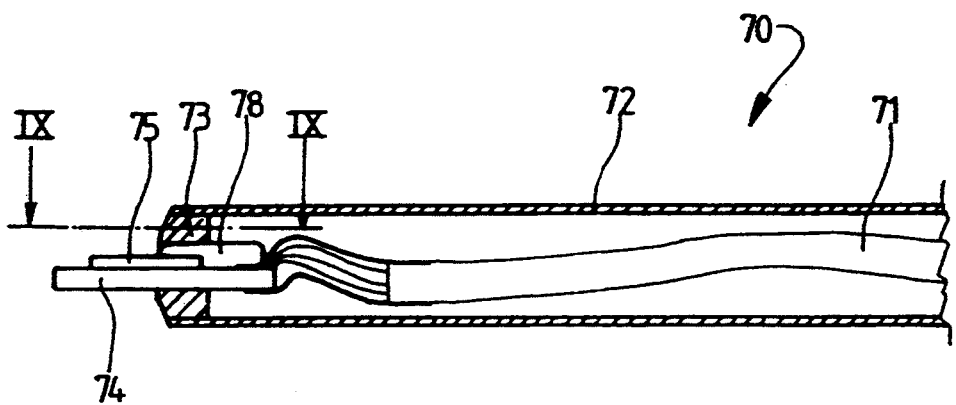
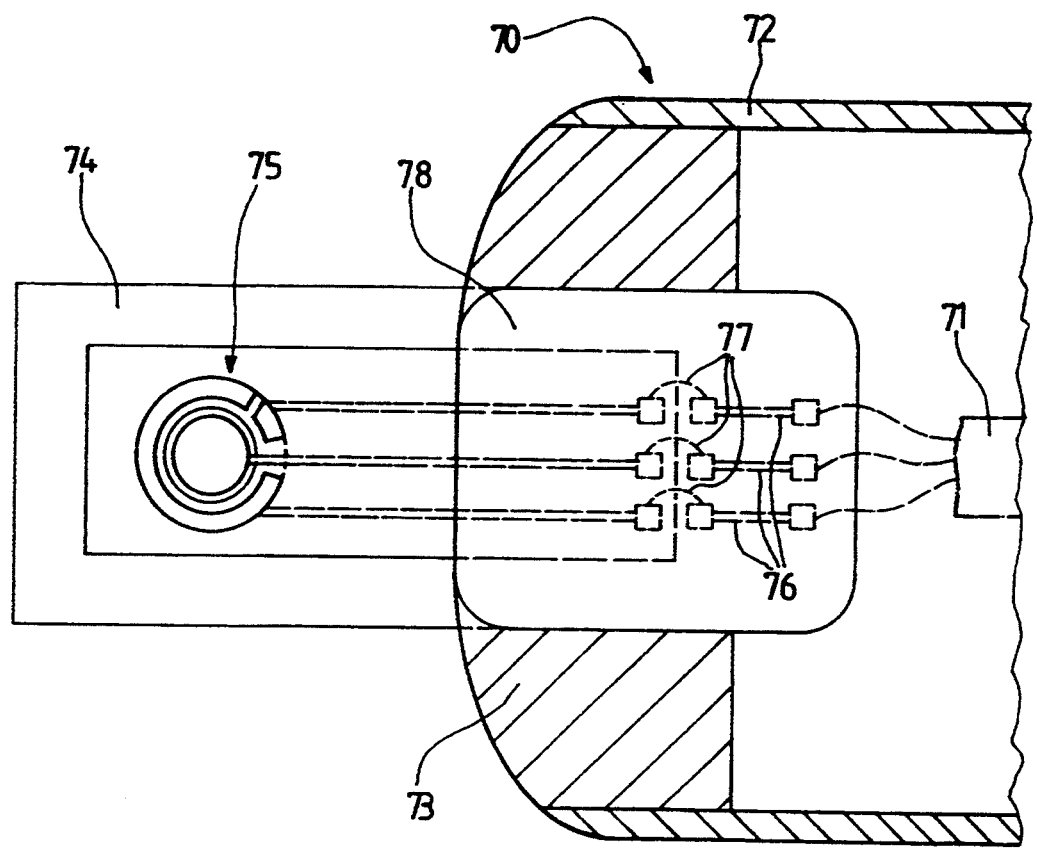
Fig. 9

AMPEROMETRIC MEASURING DEVICE HAVING AN ELECTROCHEMICAL SENSOR

BACKGROUND OF THE INVENTION

The instant invention relates to an amperometric sensor device the sensor of which forms a miniature electrochemical cell and which is intended to detect or measure the content of an oxygen reducible substance in a fluid.

Sensor devices of this type are notably, but not exclusively, used to measure the chlorine content of drinking water.

DESCRIPTION OF THE PRIOR ART

A sensor used for this purpose and its mechanism of operation are described in an article by A. v. d. Berget al., published in the journal "Transducers" 1991—International Conference on Solid State Sensors and Actuators, page 233.

The design of the sensor described in this article is shown in FIGS. 1 and 2 of the appended drawings.

A substrate 2 of silicon cut out according to appropriate photolithographic treatment from a wafer of silicon, is fixed to a printed circuit wafer 1 according to the techniques used to manufacture integrated circuits and the like.

The substrate 2 is covered with a layer 3 of silicon oxide ($SiO_2$) on which is deposited a layer 4 of an insulator such as aluminium oxide ($Al_2O_3$).

The known sensor also has three electrodes 5, 6 and 7 forming a working electrode, a counter electrode and a reference electrode respectively which are made in the form of strips deposited, also by photolithographic techniques, on the insulating layer 4.

The electrodes 5, 6 and 7 are then covered by a diffusion membrane 8 formed by an organic material such as poly HEMA hydrogel or the like (see the above-cited article). This membrane, deposited and polymerised preferably using photolithographic techniques, is designed to guarantee uniform contact without fluid turbulence of the fluid to be analysed with the electrodes.

These are individually connected to contacts 9 provided on the printed circuit 1 by means of welded wires 10, an encapsulation 11 then being placed on the assembly to protect it from the fluid to be analyzed with the exception, of course, of part of the diffusion membrane 8 and, thus of the electrodes 5, 6 and 7, so that the electrochemical reaction can take place.

It should be noted that if one wishes to measure the chlorine content of water, the electrodes 5 and 6 are made of platinum and the reference electrode 7 is of silver covered with a thin layer of silver chloride (AgCl).

The amperometric sensor device having this sensor combined to a circuit designated "potentiostat", which is connected to this latter, makes it possible to evaluate the content of oxygen reducible substance in a fluid (for example the chlorine content in water) by measuring the electric current generated at the working electrode 5 of the sensor.

Although it operates in satisfactory manner in principle, the sensor designed in this manner has certain disadvantages.

Indeed, if the dimensions of the electrodes (which are only a few millimeters long and are of the order of one tenth of a millimeter wide) can be set very accurately using photolithographic techniques, this does not apply to those of the encapsulation 11. Since this encapsulation 11 has to insulate the non-active conductive parts of the electrodes 5, 6 and 7 from the fluid to be analyzed, it should preferably overlap slightly on the hydrogel layer constituting the diffusion membrane 8. In the example shown, the overlapping zone is shown by the distance d and has a front edge 12 the exact localization of which in relation to the diffusion membrane is difficult to control accurately. In other words, the distance d can vary to a considerable degree from one sensor to another. This distance definitively determines the area of the zone exposed to the fluid and thus the active measuring surface to which the electrochemical current is generated, with the result that the intensity of this current, all other aspects being equal, will differ from one sensor to the next.

Moreover, in order to generate a sizeable electrochemical current it is desirable for this active surface to be as large as possible for the given dimensions of a sensor. Under these conditions, the front edge 12 of the encapsulation must be as close as possible to the rear edge 13 of the membrane 8. However, it is then possible that the fluid to be analyzed escapes under this edge and causes the production of leakage currents between the parts of the strips of the electrodes situated behind the membrane 8 and thus not normally supposed to take part in the production of the electrochemical measuring current.

Finally, the greatest disadvantage of the device of the prior art is that the area of the active surface of the working electrode cannot be determined accurately, with the result that each sensor has to be accurately calibrated and that the interface between the membrane and the encapsulation is a source of disturbances.

OBJECTS OF THE INVENTION

It is an object of the invention to overcome the disadvantages of the sensor device described in the above-cited article.

BRIEF SUMMARY OF THE INVENTION

The object of this invention is thus an amperometric sensor device, in particular for measuring the content of an oxygen reducible substance in a fluid, having in combination a sensor having a planar structure obtained by photolithographic techniques and a measuring circuit for measuring the intensity of the electrochemical current generated by said sensor, said structure comprising
    an insulating substrate
    a set of electrodes composed of at least one working electrode, one counter electrode and one reference electrode, at least said working electrode being disposed on said insulating substrate,
    a diffusion membrane deposited on at least part of said electrodes, and
    connection means to connect the electrodes to said measuring circuit,
    said amperometric sensor being characterised in that
    the conductive part of said working electrode, situated on the surface of said substrate being entirely covered by said diffusion membrane which overlaps this electrode over its entire peripheral zone, and,
    in that said membrane is entirely exposed so that, when the device is functioning, it is in contact over its entire surface with the fluid to be analyzed.

BRIEF DESCRIPTION OF THE INVENTION

As a result of these features, the area of the active surface of the working electrode is only defined by the area of its conducting part on the surface of the substrate, the dimensions of said area being determinable with great accuracy since they are defined during the photolithographic process conducted to create the electrode at the surface of the substrate.

Since, moreover, the diffusion membrane overlaps the working electrode over its entire peripheral zone, any amount of electrochemical current generated at the surface of the working electrode can be taken into account for the measurement with the exclusion of any leakage current.

According to another important feature of the invention, said connection means have at least one conductor connected to said working electrode and passing in said structure at a level subjacent to the active surface thereof, by extending at least beyond the periphery of said diffusion membrane.

This feature also makes it possible to avoid the conducting parts of the sensor apart from those forming its working electrode from taking part in the production of the electrochemical current, it being easily possible to cover the connection members leading from the periphery of the diffusion membrane towards the connection terminals of the sensor with the encapsulation which, in this case, cannot influence the extent of the active surface of the sensor.

BRIEF DESCRIPTION OF THE DRAWINGS

Other features and advantages of the invention will emerge from study of the following description given solely by way of example and made with reference to the appended drawings in which:

FIG. 1 is a diagrammatic section of an amperometric sensor device made according to the prior art technology;

FIG. 2 is a sectional view taken along the line II—II of FIG. 1;

FIG. 8 shows a diagrammatic view in axial section of a sensor according to a practical assembly;

FIG. 9 is a view, in larger scale than that of FIG. 8, of the sensor used in the device of FIG. 8, the view being taken along the line IX—IX thereof;

DETAILED DESCRIPTION OF THE DRAWINGS

Figure 3:
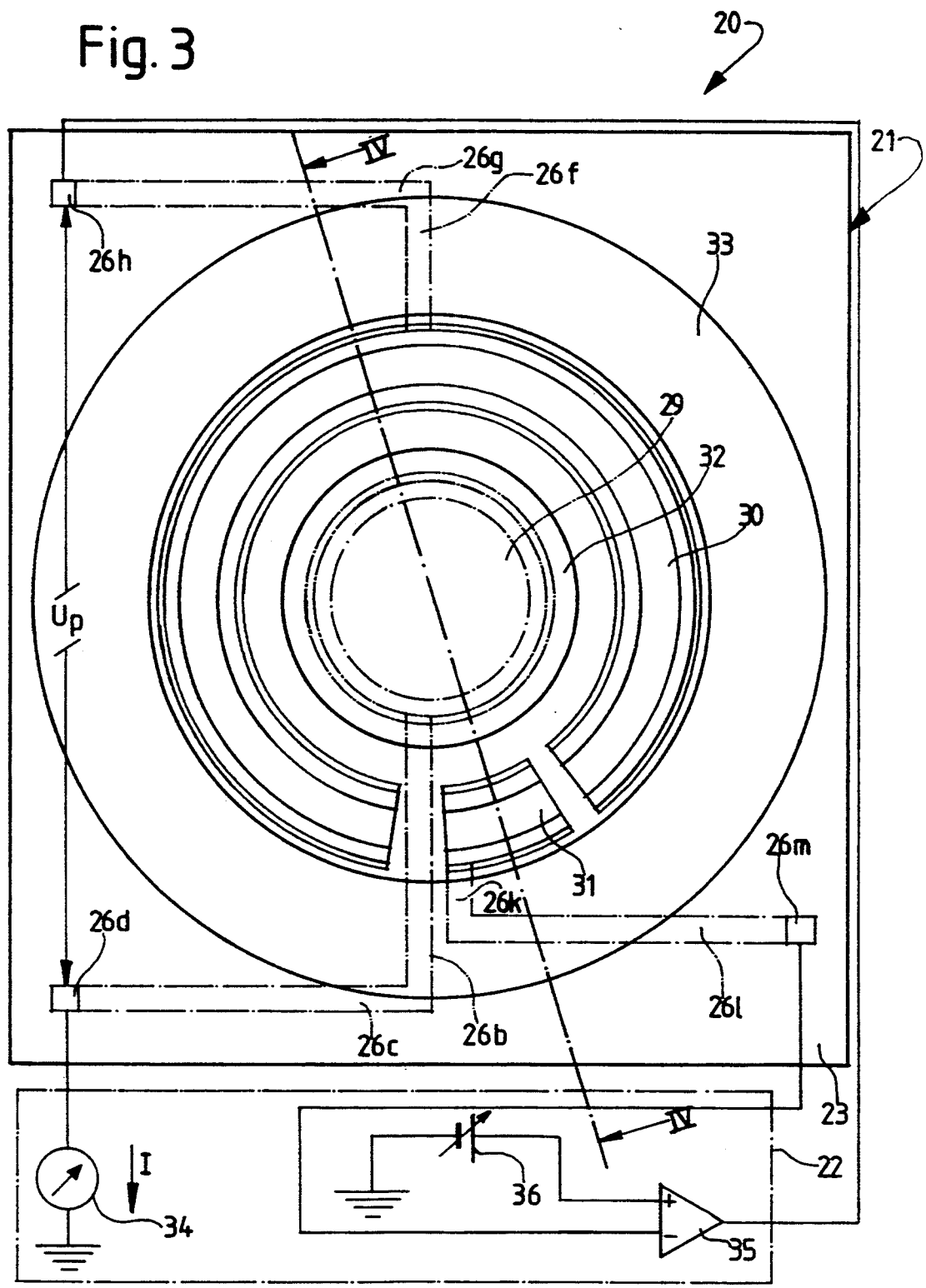
FIG. 3 is a plan view of an amperometric sensor combined with a measuring circuit to form the sensor device of the invention.
Figure 4:
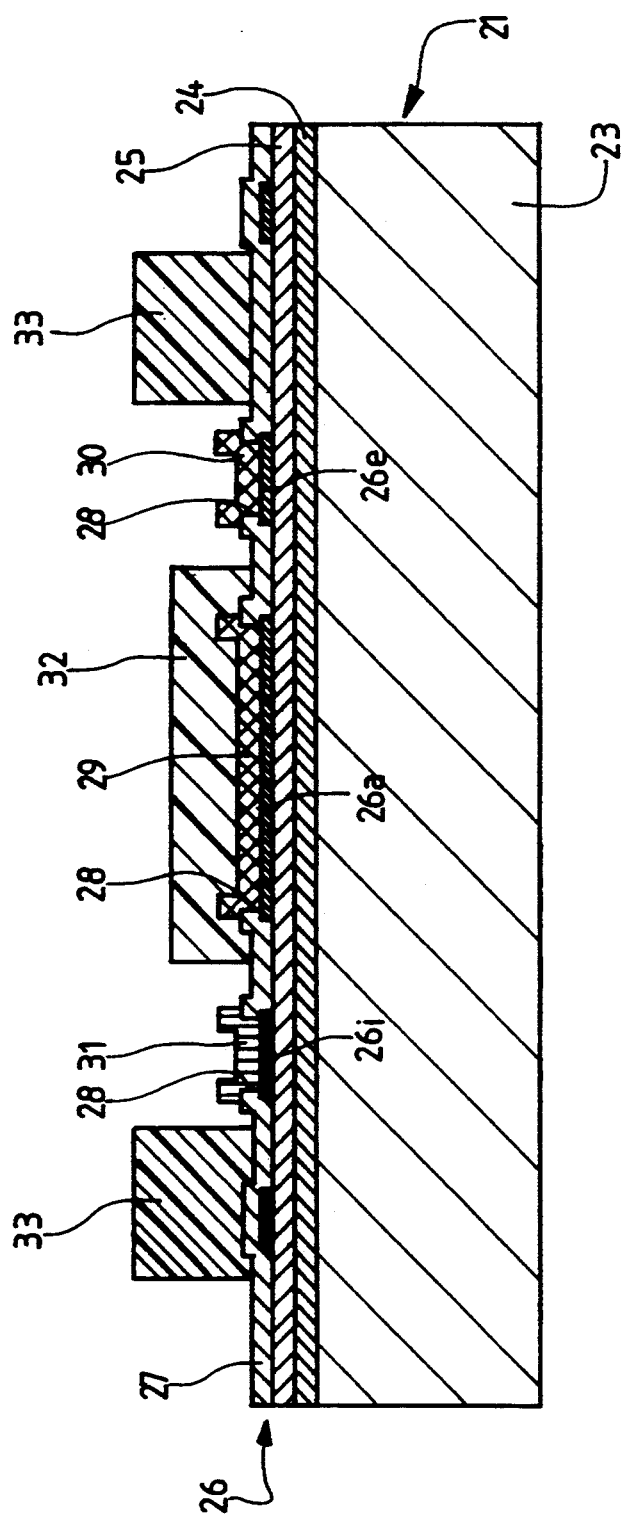
FIG. 4 is a diagrammatic section taken along the line IV—IV of FIG. 3.

Reference will now be made to FIGS. 3 and 4 which represent an amperometric sensor device 20 designed according to the preferred embodiment of the invention. This device firstly comprises the sensor per se 21, as well as a measuring circuit 22 which is shown in FIG. 3 according to an extremely simplified arrangement. FIG. 4 is a sectional view of the sensor 21 in which the thicknesses of the various layers are not shown with their exact proportions so as to make the representation clearer.

The sensor 21 has a substrate 23, of silicon for example, cut, after appropriate photolithographic treatments, from a wafer of silicon in the manner conventionally used in the technology for manufacturing semi-conductor components. The substrate 23 is covered by an insulating layer 24, preferably made of silicon oxide ($SiO_2$). This layer is in turn covered by another insulating layer 25, of silicon nitride ($Si_3N_4$) for example, to which layer is applied a configuration of connections 26 forming part of the connection means connecting the sensor per se 21 to the measuring circuit 22. The configuration of connections 26 is effected in the form of various tracks of polysilicon, the shape of which will be described below. It is covered by a third insulating layer 27 preferably made of silicon nitride ($Si_3N_4$) and in which several openings 28 are provided, the configuration of the connection thus being subjacent to the upper surface of the sensor. Each of these openings 28 has a determined shape and it receives a metal deposition designed to constitute a sensor electrode 21.

The first of these deposits thus forms the working electrode 29 of the sensor, preferably made of platinum. In the example shown, this working electrode 29 is circular in shape and is located in the centre of the wafer above a contact zone 26a of polysilicon of the connection configuration 26. As shown in FIG. 3, the contact zone 26a is connected to a polysilicon strip composed of branches 26b and 26c, the branch 26c terminating in a connection terminal 26d appearing on the upper surface of the third insulating layer 27.

A second metal deposition, preferably also of platinum, constitutes the counter electrode 30 of the sensor 21. As may also be seen in FIG. 3, this counter electrode is, in this example, arcuate and extends virtually entirely around the working electrode 29 above a polysilicon contact zone 26e which is in contact with a polysilicon conductor strip, the branches 26f and 26g of which lead to a connection contact 26h also appearing on the upper surface of the insulating layer 27.

Finally, a third metal deposition, of silver covered with a very thin layer of silver chloride (AgCl) fills the third opening provided in the insulating layer 27 and constitutes the reference electrode 31 of the sensor 21. The reference electrode is situated above a polysilicon contact zone 26i which is connected to a contact strip, also of polysilicon, composed of two branches 26k and 26l leading to a contact connection 26m appearing on the upper surface of the insulating layer 27.

The working electrode 29 is covered by a diffusion membrane 32 composed of a hydrogel preferably made of polyhydroxyethylmethacrylate (poly HEMA). The role of this membrane is described in detail in the above-cited article. Its aim is essentially to prevent turbulence in the fluid to be analyzed above the working electrode 29 and its also makes it possible to prevent dirt depositing thereon from the fluid to be measured. The chemical body which has just been indicated for the membrane is only one possible example, it being possible to use any other substance fulfilling the same role. It is nonetheless advantageous for it to be possible to deposit the substance using conventional photolithographic techniques and to be polymerised by insolation, which is the case with polyHEMA.

It will be noted that, according to an essential feature of the invention, the diffusion membrane 32 entirely covers the working electrode 29 and that it even overlaps the exterior periphery of this electrode, which makes it possible to accurately define the area of the active surface of this electrode. Moreover it will be shown below that when the sensor device of the invention is used, the membrane 32 is exposed to the fluid to be analyzed by the entirety of its uncovered surface.

FIGS. 3 and 4 also show that it is possible to add to the arrangement which has just been described a packing 33 fixed about the arrangement of the sensor electrodes on the upper surface of the insulating layer 27, it being possible for this packing to be made, for example of a polysiloxane.

Reference being made in particular to FIG. 3, it will be seen that the sensor 21 is connected to the measuring circuit 22 which forms an assembly known as a "potentiostat" (FIG. 3 shows a very simplified layout thereof). The working electrode 29 is connected via the intermediary of the contact 26d, to a current measuring instrument 34 which is also connected to earth. Reference electrode 31 is connected through contact 26m, to the inverted input of the amplifier 35. The non-inverted input of which is connected to one side of an adjustable power source 36, the other side of which is connected to ground. This source 36 makes it possible to adjust the polarisation voltage $U_p$ present between the counter electrode 30 and the working electrode 29.

The sensor 21 thus constitutes an electrochemical microcell, the electrochemical reaction with the fluid to be analyzed by virtue of the presence of the oxygen reducible substance causing the production of an electrochemical current I which can be measured using the measuring instrument 34.

The amperometric sensor device which has just been described is particularly suitable for measuring the chlorine content of drinking water, but it goes without saying that by choosing appropriate metals for the sensor electrodes and the polarisation voltage applied to the working electrode it would be possible, on the basis of the same inventive concept, to produce sensor devices capable of detecting substances other than chlorine in water or in fluids other than water.

FIG. 3 clearly shows the essentially circular arrangement of the electrodes 29, 30 and 31. This arrangement is very advantageous in that it leads to the best occupation of the substrate surface 23 for a maximum surface of the working electrode 29, the area of which essentially determines the intensity of the measuring current.

However, specialists in the relevant technology will understand that the configuration obtained by photolithography on the substrate 23 can be different from that shown in FIGS. 3 and 4, always assuming, of course, that the essential features of the invention are present, namely on the one hand the total covering by the diffusion membrane 32 of the working electrode 29 and, on the other hand, the total exposure of the diffusion membrane 32 to the fluid to be analyzed.

Solely by way of indication, the following dimensions and thicknesses are appropriate for producing the sensor device that has just been described:

Dimensions of substrate 23 : 4 mm×4.4 mm
Surface of working electrode : 1.54 mm2
Surface of counter electrode : 1.37 mm2
Surface of reference electrode : 0.16 mm2
Thickness of substrate 23 : 380 u
Thickness of insulating layer 24 : 6000 Å
Thickness of insulating layer 25 : 2000 Å
Thickness of insulating layer 27 : 2000 Å
Thickness of the polysilicon conducting tracks forming the connection means of the electrodes : 1500 Å
Thickness of the electrodes : 3000 Å
Thickness of the diffusion membrane: 50 u
Thickness of the polysiloxane barrier : 200 u.

FIGS. 3 and 4 also show that only the surfaces of the membrane, of the counter electrode and of the reference electrode, used for the measurement are in contact with the fluid to be analyzed, to the exclusion of all other connection means which connect the electrodes to the measuring circuit 22. Indeed, as will be seen hereinbelow, thanks to the presence of the packing 33, it is easily possible to seal the measuring zone tight (that is the zone in which the electrodes are located), from the space above the remainder of the substrate 23, and notably that in which are located the visible contacts 26d, 26m and 26h which are used to make the electrical connection of tile sensor 21 with the measuring circuit 22. Thus, no conducting element can disturb the measurement due to current leakage or other disturbing cases, as was the case in the devices of the prior art.

Figure 5:
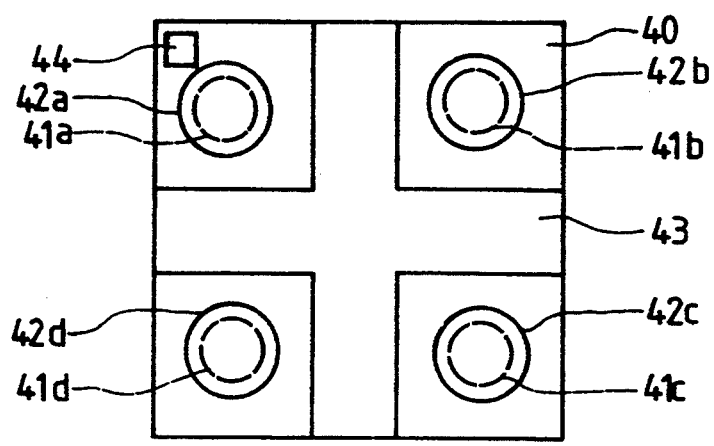
FIGS. 5, 6 and 7 are diagrammatic plan views of three other configurations of the sensor capable of being used in the sensor device of the invention.
Figure 6:
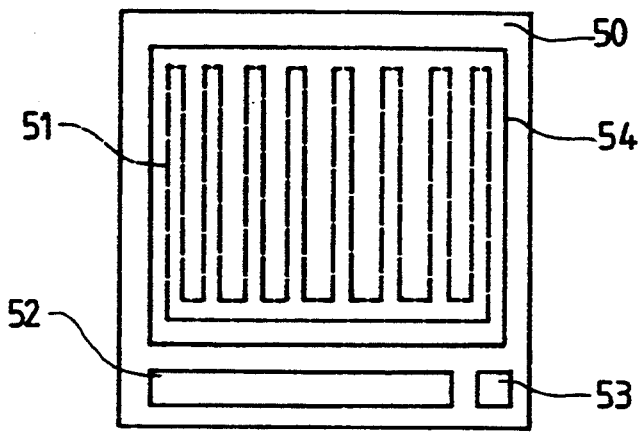
Figure 7:
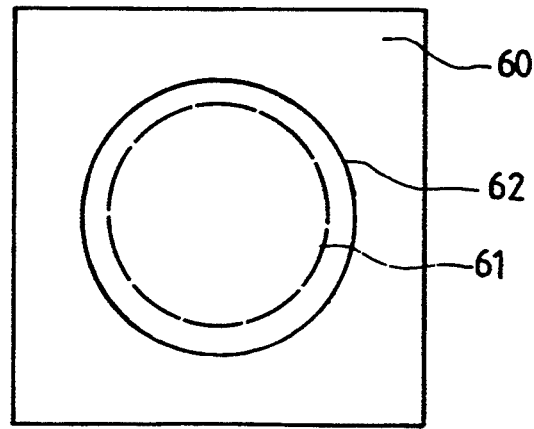

FIGS. 5, 6 and 7 show three different examples of electrode configurations capable of being used on the substrate of the amperometric sensor.

In FIG. 5, a substrate 40 has four constituent working electrodes 41a to 41d arranged at the four corners of the surface of the substrate and each covered by a separate diffusion membrane 42a to 42d. A counter electrode 43 in the shape of a cross is also present on the substrate as well as a reference electrode 44 which is placed close to one of the substrate angles. A sensor of this type is manufactured using techniques very similar to those used to make the sensor shown in FIGS. 3 and 4 and further reference will therefore not be made thereto.

It should simply be noted that in this embodiment of the invention, each separate membrane 42a to 42d is arranged in the same manner as the diffusion membrane of FIGS. 3 and 4 and consequently the same favourable results inherent to the invention are obtained here.

In FIG. 6, a substrate 50 has a comb-shaped working electrode 51, the teeth of which extend parallel to one another towards one of the edges of the substrate and contiguous to which there is a counter electrode 52 which extends along the opposite edge of the substrate 50. A reference electrode 53 is provided close to one of the angles thereof. The comb-shaped working electrode 51 is covered by a diffusion membrane 54.

FIG. 7 shows another embodiment in which it is proposed that the counter electrode and the reference electrode are physically separated from the substrate 60 on which only one working electrode 61 is provided, produced in the same manner as that of FIGS. 3 and 4. A diffusion membrane 62 covers the electrode 61 by overlapping its outer periphery.

FIGS. 8 and 9 show a first practical application of the amperometric sensor device of the invention.

As shown in FIG. 8, this refers to a stylus 70 capable of being connected by a cable 71 to a housing (not shown) containing the measuring circuit, this assembly capable of being used to regularly measure the gas content of a fluid. An assembly of this kind could be made portable and easily handled, for example for use during verification of the chlorine content of the water in a swimming pool.

More precisely, a small tube 72, forming a casing and made for example of aluminium, has at one of its ends a stopper 73 with a support 74 mounted therein. Fixed to this support is a sensor 75 of the type of that shown by 21 in FIGS. 3 and 4. As shown in FIG. 9, the support 74 is a printed circuit having three connection tracks 76 which are connected to the three electrodes of the sensor respectively, via the intermediary of welded wires 77.

As may be seen, in this case the packing 33 of FIGS. 3 and 4 is replaced by a flange 78 of an insulating material which is placed on the sensor substrate 75, the sensor electrodes and in particular the working electrode covered by its diffusion membrane being exposed to the fluid to be analyzed when the stylus 70 is immersed therein. In contrast, all the other conducting members, and notably the connection contacts ensuring the coupling with the measuring circuit are covered herein by the flange 78.

The aluminium tube 72 is traversed by the cable 71 which is a three-wire connection establishing the link between the support 74 and the measuring circuit (not shown in these figures).

Figure 10:
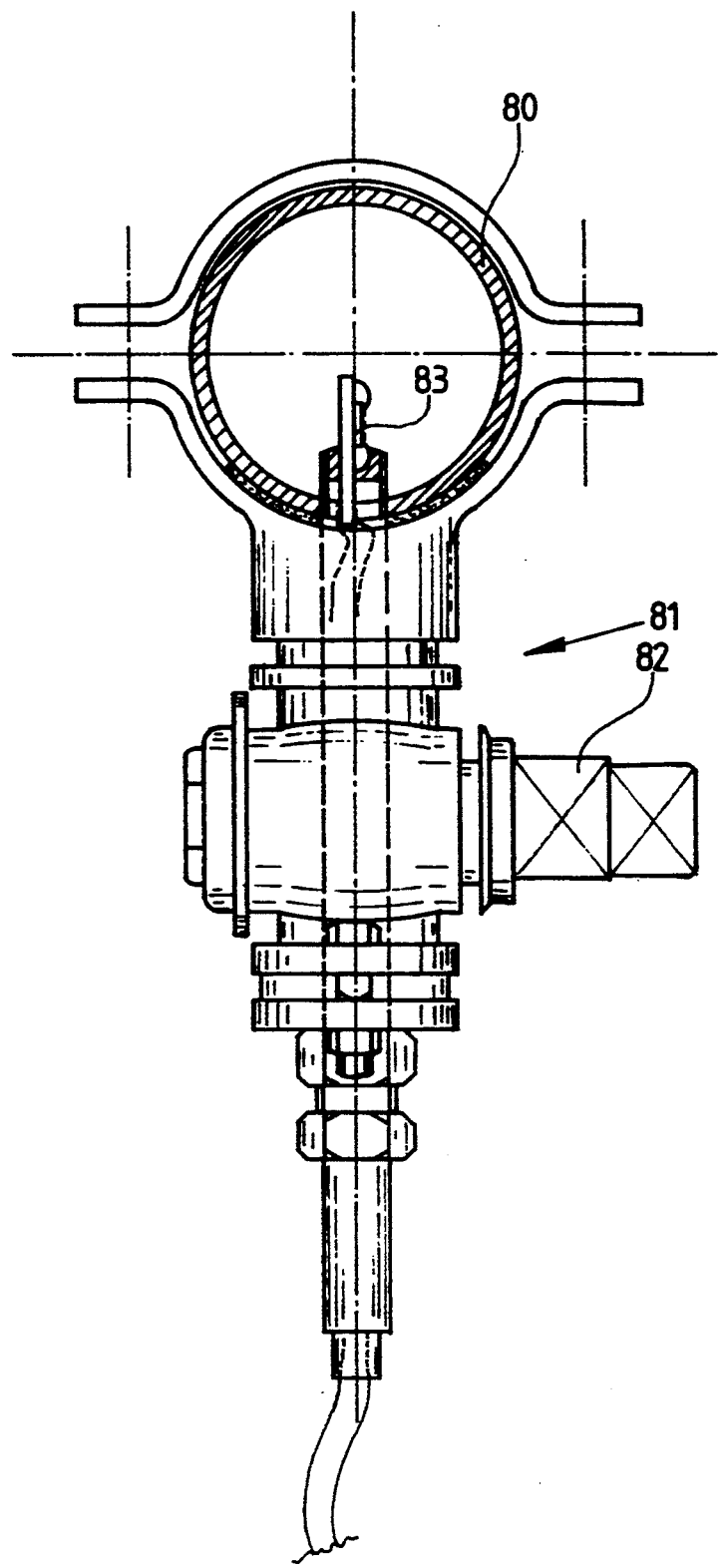
FIG. 10 shows an embodiment of the sensor of FIGS. 8 and 9.

FIG. 10 shows another way of using this amperometric sensor device according to the invention for purposes of continuous monitoring of the content of oxygen reducible substance in a fluid circulating in piping 80. Fixed to this piping 80 is a support 81 comprising a tap 82 across which an amperometric sensor device of the type shown in FIGS. 8 and 9 can be positioned. The measuring device can easily be located in the piping or be removed therefrom by turning the tap 82, without fluid escaping from the piping.

Figure 11:
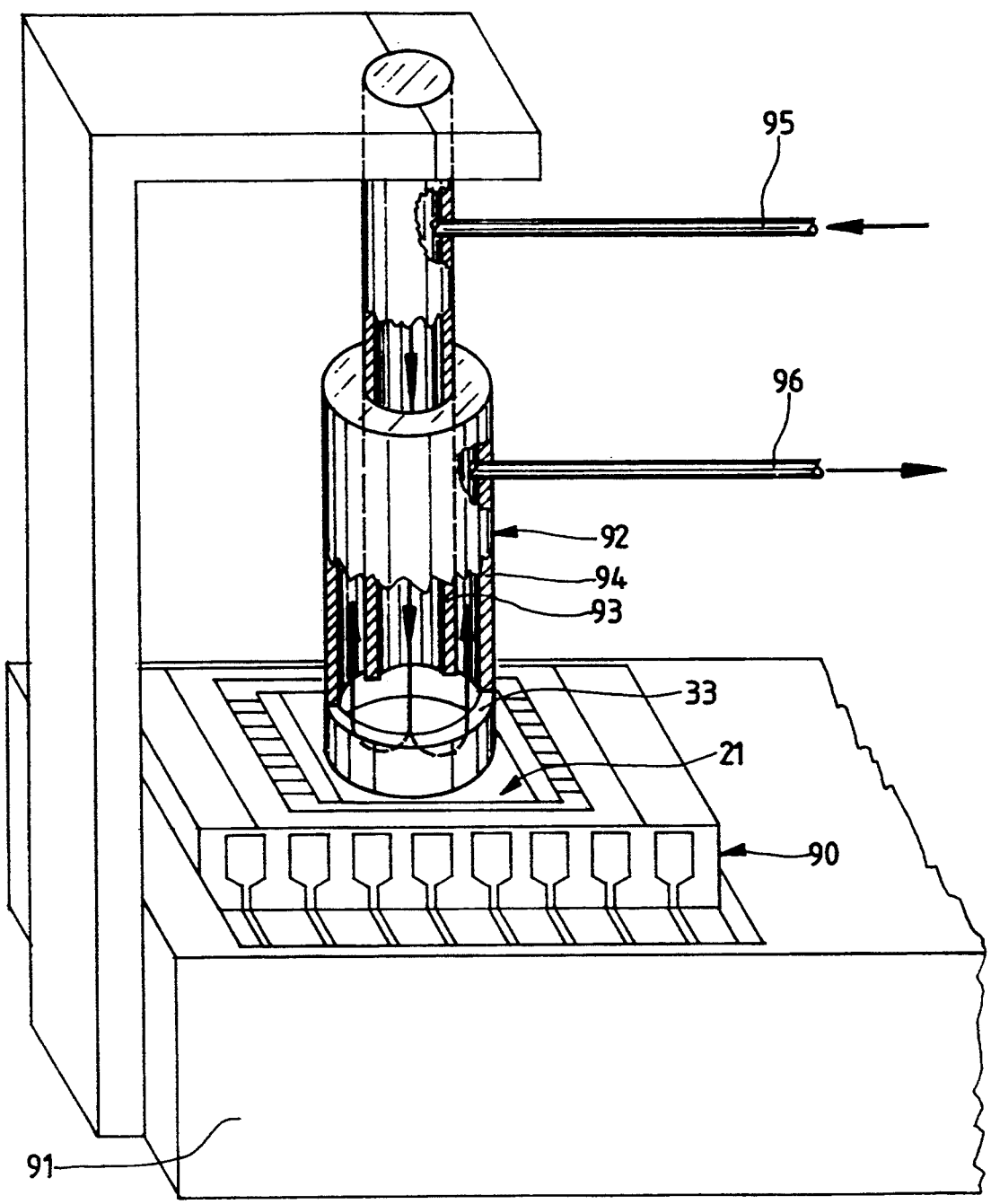
FIG. 11 shows another application of the sensor device of the invention.

FIG. 11 shows another way of using the sensor device of the invention. In this case the sensor has been encapsulated, its construction being identical to that of FIGS. 3 and 4, in a standardized housing 90 of the DIL type with sixteen pins normally used for integrated circuit components. The housing 90 is placed for example on a bracket-shaped support 91 to which is fixed a cylindrical tubular member 92 with two concentric channels 93 and 94 to which two conduits 95 and 96 respectively are connected that are designed to be connected to input and output tubes (not shown) of the fluid to be analyzed.

As may be seen from FIG. 11, the outer tube 97 of tubular member 92 abuts against the packing 33 which surrounds the active part of the sensor 21 whereas the extremity of an inner tube 98 is slightly offset in relation to the active surface of the diffusion membrane.

The fluid to be analyzed can therefore continuously flow in the inlet conduit 95, through the inner channelling 93, across the chamber provided above the diffusion membrane and through the outer channelling 94 towards the outlet conduit 96. Under these conditions, the amperometric device according to the invention can therefore deliver a permanent signal which is a direct function of the oxygen reducible substance content in the fluid to be analyzed. The signal in question can, of course, be made use of in any suitable manner, for example it may serve to trigger a warning when the oxygen reducible substance content exceeds a permitted value, to serve as actual value in an adjustment loop designed to control the oxygen reducible substance content as a function of the difference between this value and a reference value, etc.

I claim:

1. An amperometric sensor device for measuring the content of an oxygen reducible substance in a liquid, having in combination a sensor having a planar structure obtained by photolithograpic techniques and a circuit for measuring the intensity of the electrochemical current generated by said sensor, said structure comprising
    an insulating substrate
    a set of electrodes composed of at least one working electrode., one counter electrode and one reference electrode, at least said working electrode being disposed on said insulating substrate,
    said working electrode having an active surface only defined by a conductive part at the surface of said substrate, said device further comprising a diffusion membrane covering said conductive part of said working electrode While Overlapping the entire periphery of said conductive part, and
    connection means to connect said electrodes to said measuring circuit,
    said diffusion membrane, said reference electrode and said counter electrode being entirely exposed so that, when said device is functioning, they are in contact over their entire surfaces with the liquid to be analyzed.

2. An amperometric device according to claim 1, wherein said connection means includes at least one conductor connected to said working electrode and disposed on said insulating substrate at a level below the active surface of the working electrode and, extending beyond the periphery of said diffusion membrane.

3. An amperometric device according to claim 2, wherein the working electrode has a substantially circular shape.

4. An amperometric device according to claim 3, wherein said counter electrode and/or said reference electrode are arcuate in form and disposed concentrically about the working electrode.

5. An amperometric device according to claim 1, wherein the working electrode has a substantially circular shape.

6. An amperometric device according to claim 5, wherein said counter electrode and/or said reference electrode are arcuate in form and disposed concentrically about the working electrode.

7. An amperometric device according to claim 1, wherein said set of electrodes is surrounded by a packing fixed to said substrate and in that said connection means comprise liaison contacts with said measuring circuit situated outside the perimeter of said packing at the surface of said substrate.

8. An amperometric device according to claim 1, wherein said sensor is mounted on a printed circuit mounted in turn in a metal tube forming a casing and traversed by part of the connection means.

9. An amperometic device according to claim 1, wherein said sensor is disposed in a housing having the shape of a standardized DIL encapsulation housing for integrated circuits.

10. An amperometric device according to claim 1, further comprising a cylindrical tubular member having concentric inner and an outer tubes and two concentric channels respectively for communicating with one inlet and one outlet of the fluid to be analyzed, a packing and a support arranged to hold said tube abutting against said packing by one of the extremities of the outer tube.

11. An amperometric device according to claim 1, wherein said working electrode has several elements distributed on said substrate and in that said diffusion membrane has several elements covering respectively the elements of said working electrode by individually overlapping in relation to these electrode elements.

12. An amperometric device according to claim 1, wherein said working electrode has the shape of a comb.

* * * * *